United States Patent
Ikeda et al.

(10) Patent No.: US 6,235,823 B1
(45) Date of Patent: May 22, 2001

(54) CRYSTALLINE POLYPROPYLENE RESIN COMPOSITION AND AMIDE COMPOUNDS

(75) Inventors: Naoki Ikeda; Masafumi Yoshimura, both of Kyoto-fu; Kazuaki Mizoguchi, Jyoyo; Hiroshi Kitagawa; Yuji Kawashima, both of Otsu; Kiyoshi Sadamitsu, Yawata; Yasuyuki Kawahara, Jyoyo, all of (JP)

(73) Assignee: New Japan Chemical Co., Ltd., Kyoto (JP)

( * ) Notice: Subject to any disclaimer, the term of this patent is extended or adjusted under 35 U.S.C. 154(b) by 0 days.

(21) Appl. No.: 08/003,659

(22) Filed: Jan. 13, 1993

(30) Foreign Application Priority Data

| Jan. 24, 1992 | (JP) | 4-034088 |
|---|---|---|
| Apr. 27, 1992 | (JP) | 4-135892 |
| Sep. 28, 1992 | (JP) | 4-283689 |
| Nov. 9, 1992 | (JP) | 4-324807 |

(51) Int. Cl.⁷ .................. C08K 5/20; C08K 5/21
(52) U.S. Cl. .................. 524/229; 524/214; 564/152; 564/155; 564/180
(58) Field of Search .................. 524/214, 229; 564/152, 155, 180

(56) References Cited

U.S. PATENT DOCUMENTS

| 3,499,884 | | 3/1970 | Wood . | |
|---|---|---|---|---|
| 4,322,503 | * | 3/1982 | Chatterjee | 524/229 |
| 4,394,474 | * | 7/1983 | McKinney et al. | 524/232 |
| 4,530,952 | * | 7/1985 | Tayama et al. | 524/229 |
| 4,607,072 | * | 8/1986 | Su | 524/229 |
| 4,684,684 | * | 8/1987 | Abe et al. | 524/229 |

FOREIGN PATENT DOCUMENTS

| 695 506 | | 9/1967 | (DE) . | |
|---|---|---|---|---|
| 32 06 138 | | 9/1983 | (DE) . | |
| 32 06 138 A1 | | 9/1983 | (DE) . | |
| 0 079 506 | | 5/1983 | (EP) . | |
| 0 263 678 | | 4/1988 | (EP) . | |
| 0 263 678 A3 | | 4/1988 | (EP) . | |
| 2 656 620 | | 7/1991 | (FR) . | |
| 20718 | * | 10/1963 | (JP) | 524/229 |

* cited by examiner

Primary Examiner—Kriellion Sanders
(74) Attorney, Agent, or Firm—Armstrong, Westerman, Hattori, McLeland & Naughton, LLP

(57) ABSTRACT

Disclosed are a crystalline polypropylene resin composition comprising a crystalline polyproplylene resin and a β-nucleating agent, and a method of increasing the proportion of β-form crystals in a crystalline polypropylene resin molding comprising molding the composition, the β-nucleating agent being a diamide compound.

21 Claims, No Drawings

CRYSTALLINE POLYPROPYLENE RESIN COMPOSITION AND AMIDE COMPOUNDS

FIELD OF THE INVENTION

The present invention relates to a crystalline polypropylene resin composition containing an amide compound capable of acting as a nucleating agent for predominant formation of the β-crystal form and to a novel amide compound which is of use as a nucleating agent for the formation of the β-crystal form.

PRIOR ART

It is known that crystalline polypropylene may occur in α, β, γ and δ crystal forms as well as in the smectic crystal form which is formed on quenching of melted polypropylene. The β-crystal form (hereinafter referred to as "β-form") differs from the a-form which is found in the conventional natural pellet in that it is lower in melting point and in density, not to speak of differences in the mode of crystallization and of fracture, thus being of interest from application points of view (Kobunshi Kagaku 30, 694-698, (1973)).

For the production of crystalline polypropylene containing the β-form, a process comprising crystallizing molten polypropylene on a temperature gradient and a process comprising blending with a small amount of a nucleating agent (hereinafter referred to as "β-nucleating agent") are known. Since the former process is time-consuming and provides only a low yield, the latter process employing a β-nucleating agent is more advantageous for all practical purposes.

As such a β-nucleating agent, γ-quinacridone is well-known (Polymer Letters, 6, 539-546, (1968)). However, this nucleating agent has the drawback that it imparts a red tint to the product and requires special apparatus and operation for blending it with the polymer.

SUMMARY OF THE INVENTION

The object of the present invention is to provide a novel β-nucleating agent insuring an efficient production of a product containing β-crystalline polypropylene in a large amount and much improved in the aspect of product color because of substantial absence of coloring property, and to provide a practically useful crystalline polypropylene resin composition containing said β-nucleating agent.

The inventors of the present invention discovered, after extensive research to provide a β-nucleating agent that would solve the above-mentioned problems, that a class of amide compounds having a specific chemical structure can accomplish the above object and that some of said amide compounds are novel compounds which are not described before in the published literature. The present invention has been achieved on the basis of the above findings.

The crystalline polypropylene resin composition of the present invention is characterized in that, in addition to a crystalline polypropylene resin, it contains at least one β-nucleating agent selected from the group consisting of amide compounds of the formula (1), amide compounds of the formula (2) and amide compounds of the formula (3) to be described below in an amount effective for increasing the content of the β-crystal form:

(1) an amide compound of the formula:

$$R^2-NHCO-R^1-CONH-R^3 \quad (1)$$

wherein $R^1$ is a residue of a $C_{3-20}$ saturated or unsaturated aliphatic dicarboxylic acid, a residue of a $C_{6-30}$ saturated or unsaturated alicycic dicarboxylic acid or a residue of a $C_{8-30}$ aromatic dicarboxylic acid; $R^2$ and $R^3$ are the same or different and each represents a $C_{3-12}$ cycloalkyl group, a $C_{3-12}$ cycloalkenyl group, or a group of the formula

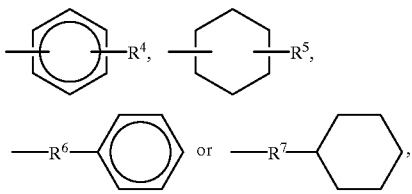

wherein $R^4$ is a hydrogen atom, a $C_{1-12}$ straight- or branched-chain alkyl group, a $C_{2-12}$ straight- or branched-chain alkenyl group, a $C_{6-10}$ cycloalkyl group or a phenyl group; $R^5$ is a $C_{1-12}$ straight- or branched-chain alkyl group, a $C_{2-12}$ straight- or branched-chain alkenyl group, a $C_{6-10}$ cycloalkyl group or a phenyl group; and $R^6$ and $R^7$ each represents a $C_{1-4}$ straight- or branched-chain alkylene group; with the proviso that when $R^4$ is a hydrogen atom, a $C_{1-12}$ alkyl group or a $C_{6-10}$ cycloalkyl group, $R^1$ is a residue of a $C_6$ or $C_8$ saturated aliphatic dicarboxylic acid, (2) an amide compound of the formula:

$$R^9-CONH-R^8-NHCO-R^{10} \quad (2)$$

wherein $R^8$ is a residue of a $C_{4-28}$ alicyclic diamine, a residue of a $C_{4-14}$ heterocyclic diamine or a residue of a $C_{6-28}$ aromatic diamine; $R^9$ and $R^{10}$ are the same or different and each represents a $C_{3-12}$ cycloalkyl group, a $C_{3-12}$ cycloalkenyl group, or a group of the formula

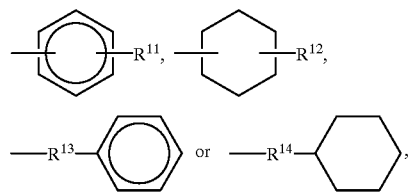

wherein $R^{11}$ is a hydrogen atom, a $C_{1-12}$ straight- or branched-chain alkyl group, a $C_{2-12}$ straight- or branched-chain alkenyl group, a $C_{6-10}$ cycloalkyl group or a phenyl group; $R^{12}$ is a $C_{1-12}$ straight- or branched-chain alkyl group, a $C_{2-12}$ alkenyl group, a $C_{6-10}$ cycloalkyl group or a phenyl group; and $R^{13}$ and $R^{14}$ each represents a $C_{1-4}$ straight- or branched-chain alkylene group; with the proviso that $R^8$ is not

(3) an amide compound of the formula:

$$R^{16}-CONH-R^{15}-CONH-R^{17} \quad (3)$$

wherein $R^{15}$ is a residue of a $C_{2-29}$ saturated or unsaturated aliphatic amino acid, a residue of a $C_{7-13}$ saturated or unsaturated alicyclic amino acid or a residue of a $C_{7-15}$ aromatic amino acid; $R^{16}$ and $R^{17}$ are the same or different and $R^{16}$ has the same meaning as $R^9$ or $R^{10}$ in the formula (2) and $R^{17}$ has the same meaning as $R^2$ or $R^3$ in the formula (1).

The present invention also provides a method for increasing the proportion of the β-crystal form in a crystalline polypropylene resin molded product which comprises molding the composition comprising a crystalline polypropylene resin and containing at least one amide compound of the above formulas (1), (2) and (3) in an amount effective for increasing the proportion of the β-crystal form.

Among these amide compounds of the formulas (1), (2) and (3), the compounds of the formula (1) and those of the formula (2) are preferred. Particularly preferred are amide compounds of the formula (1) wherein $R^1$ is —$(CH_2)_4$—,

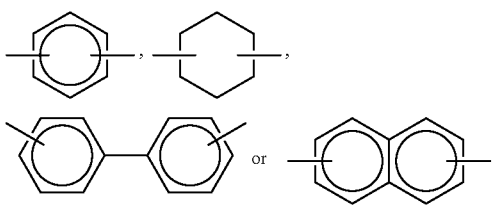

and $R^2$ and $R^3$ are the same or different and each represents a $C_{6-8}$ cycloalkyl group or represents a phenyl group substituted by a $C_{1-4}$ alkyl or cyclohexyl group, and amide compounds of the formula (2) wherein $R^8$ is

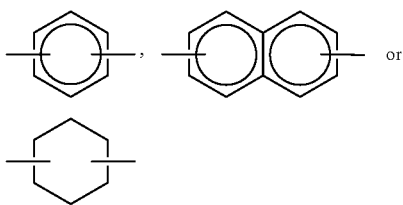

and $R^9$ and $R^{10}$ are the same or different and each is a cyclohexyl group or a phenyl group.

DETAILED DESCRIPTION OF THE INVENTION

Processes for the production of amide compounds of the formulas (1), (2) and (3) are described below.

Amide compounds of the formula (1)

The amide compound of the formula (1) can be easily prepared by subjecting an aliphatic, alicyclic or aromatic dicarboxylic acid of the the formula:

HOOC—$R^1$—COOH      (1a)

wherein $R^1$ is as defined hereinbefore to amidation reaction with an alicyclic or aromatic monoamine of the formula:

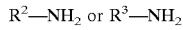

$R^2$—$NH_2$ or $R^3$—$NH_2$ wherein $R^2$ and $R^3$ are as defined hereinbefore.

This amidation reaction can be carried out in a conventional manner and any one of the following processes may be mentioned as typical examples. Incidentally, where $R^2$ and $R^3$ in the formula (1) are dissimilar to each other, a substantially equimolar mixture of the corresponding two kinds of monoamines is employed.

(i) In an inert solvent, said dicarboxylic acid is reacted with said monoamine at a temperature of about 60 to 200° C. for about 2 to 8 hours. The monoamine is generally used in an amount of about 2 to 10 equivalents per one equivalent of the dicarboxylic acid. In this process, an activator is preferably used to accelerate the reaction. The activator that can be used includes phosphorus pentaoxide, polyphosphoric acid, phosphorus pentaoxide-methanesulfonic acid, phosphorous ester (e.g. triphenyl phosphite)-pyridine, phosphorous ester-metal salt (e.g. lithium chloride), triphenylphosphine-hexachloroethane and so on. Generally, about one mole of the activator is used per mole of the dicarboxylic acid.

(ii) In an inert solvent, dichloride of said dicarboxylic acid is reacted with said monoamine at a temperature of about 0 to 100° C. for about 1 to 5 hours. The monoamine is used generally in an amount of 2 to 3 equivalents per one equivalent of the dicarboxylic acid dichloride.

(iii) In an inert solvent, a diester, particularly a di($C_{1-3}$) alkyl ester, of said dicarboxylic acid is reacted with said monoamine in the presence of a catalyst at about 0–150° C. for about 3 to 10 hours. The monoamine is used generally in an amount of about 2 to 20 equivalents per one equivalent of the dicarboxylic acid diester. The catalyst may be an acid or basic catalyst that is conventionally used in ester-amide interchange reactions, and is preferably a basic catalyst. Thus, there may be mentioned lithium, sodium, potassium; alkali metal hydrides such as lithium hydride, sodium hydride, potassium hydride, etc.; alkali metal hydroxides such as lithium hydroxide, sodium hydroxide, potassium hydroxide etc.; metal alkoxides such as sodium methoxide, sodium ethoxide, potassium tert-butoxide, etc.; and alkali metal amides such as sodium amide, lithium dipropylamide, etc., among others. The catalyst is used generally in an equimolar amount relative to said dicarboxylic acid.

The inert solvent which can be used for the above processes (i), (ii) and (iii) include, among others, benzene, toluene, xylene, chloroform, chlorobenzene, dichlorobenzene, tetrahydrofuran, dioxane, acetonitrile, N,N-dimethylformamide, N,N-dimethylacetamide and N-methylpyrrolidone.

As the dicarboxylic acid of the formula (1a) for use in said processes (i), (ii) and (iii), there may be mentioned the aliphatic, alicyclic or aromatic dicarboxylic acid corresponding to $R^1$. Thus, $R^1$ is preferably a residue formed by elimination of the two carboxyl groups of one of the following aliphatic, alicylic and aromatic dicarboxylic acids.

The aliphatic dicarboxylic acid specifically includes $C_{3-20}$, preferably $C_{3-14}$ saturated or unsaturated aliphatic dicarboxylic acids, such as malonic acid, diphenylmalonic acid, succinic acid, phenylsuccinic acid, diphenylsuccinic acid, glutaric acid, 3,3-dimethylglutaric acid, adipic acid, pimelic acid, suberic acid, azelaic acid, sebacic acid, 1,12-dodecanedioic acid, 1,14-tetradecanedioic acid, 1,18-octadecanedioic acid and so on.

The alicyclic dicarboxylic acid specifically includes $C_{6-30}$, preferably $C_{8-12}$ saturated or unsaturated alicyclic dicarboxylic acids such as 1,2-cyclohexane di-carboxylic acid, 1,4-cyclohexanedicarboxylic acid, 1,4-cyclohexanediacetic acid and so on.

The aromatic dicarboxylic acid specifically includes $C_{8-30}$, preferably $C_{8-22}$ aromatic dicarboxylic acids such as p-phenylenediacetic acid, p-phenylenediethanoic acid, phthalic acid, 4-tert-butylphthalic acid, isophthalic acid, 5-tert-butylisophthalic acid, terephthalic acid, 1,8-naphthalic acid, 1,4-naphthalenedicarboxylic acid, 2,6-naphthalenedicarboxylic acid, 2,7-naphthalenedicarboxylic acid, diphenic acid, 3,3'-biphenyldicarboxylic acid, 4,4'-biphenyldicarboxylic acid, 4,4'-binaphthyldicarboxylic acid, bis(3-carboxyphenyl)-methane, bis(4-carboxyphenyl) methane, 2,2-bis(3-carboxyphenyl)propane, 2,2-bis(4-carboxyphenyl)propane, 3,3'-sulfonyldibenzoic acid, 4,4'-sulfonyldibenzoic acid, 3,3'-oxydibenzoic acid, 4,4'- oxydibenzoic acid, 3,3'-carbonyldibenzoic acid, 4,4'-carbonyldibenzoic acid, 3,3'-thiodibenzoic acid, 4,4'-thiodibenzoic acid, 4,4'-(p-phenylenedioxy)dibenzoic acid, 4,4'-isophthaloyldibenzoic acid, 4,4'-terephthaloyldibenzoic acid, dithiosalicylic acid and so on.

On the other hand, the monoamine to be used in processes (i), (ii) and (iii) is the alicyclic or aromatic amonoamine corresponding to $R^2$ or $R^3$, i.e., $R^2$—$NH_2$ or $R^3$—$NH_2$.

The alicyclic monoamine particularly includes $C_3$–$C_{12}$ cycloalkylamines, $C_3$–$C_{12}$ cycloalkenylamines,

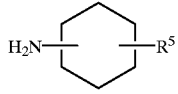

(wherein $R^5$ is as defined above),

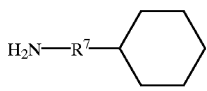

(wherein $R^7$ is as defined above) and the like, and specifically includes, among others, cyclopropylamine, cyclobutylamine, cyclopentylamine, cyclohexylamine, 2-methylcyclohexylamine, 3-methylcyclohexylamine, 4-methylcyclohexylamine, 2-ethylcyclohexylamine, 4-ethylcyclohexylamine, 2-propylcyclohexylamine, 2-isopropylcyclohexylamine, 4-propylcyclohexylamine, 4-isopropylcyclohexylamine, 2-tert-butylcyclohexylamine, 4-n-butylcyclohexylamine, 4-isobutylcyclohexylamine, 4-sec-butylcyclohexylamine, 4-tert-butylcyclohexylamine, 4-n-amylcyclohexylamine, 4-isoamylcyclohexylamine, 4-sec-amylcyclohexylamine, 4-tert-amylcyclohexylamine, 4-hexylcyclohexylamine, 4-heptylcyclohexylamine, 4-octylcyclohexylamine, 4-nonylcyclohexylamine, 4-decylcyclohexylamine, 4-undecylcyclohexylamine, 4-dodecylcyclohexylamine, 4-cyclohexylcyclohexylamine, 4-phenylcyclohexylamine, cycloheptylamine, cyclododecylamine, cyclohexylmethylamine, α-cyclohexylethylamine, β-cyclohexylethylamine, α-cyclohexylpropylamine, β-cyclohexylpropylamine, γ-cyclohexylpropylamine and so on.

The aromatic monoamine particularly includes

(where(wherein $R^4$ is as defined above),

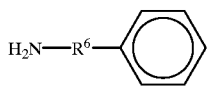

(wherein $R^6$ is as defined above) and the like, and specifically includes, among others, aniline, o-toluidine, m-toluidine, p-toluidine, o-ethylaniline, p-ethylaniline, o-propylaniline, m-propylaniline, p-propylaniline, o-cumidine, m-cumidine, p-cumidine, o-tert-butylaniline, p-n-butyl-aniline, p-isobutylaniline, p-sec-butylaniline, p-tert-butylaniline, p-n-amylaniline, p-isoamylaniline, p-sec-amylaniline, p-tert-amylaniline, p-hexylaniline, p-heptylaniline, p-octylaniline, p-nonylaniline, p-decylaniline, p-undecylaniline, p-dodecylaniline, p-cyclohexylaniline, o-aminodiphenyl, m-aminodiphenyl, p-aminodiphenyl, p-aminostyrene, benzylamine, α-phenylethylamine, β-phenylethylamine, α-phenylpropylamine, β-phenylpropylamine and γ-phenylpropylamine.

Among the amide compounds of the formula (1), the compounds which can be specifically represented by the following formula (4) are novel compounds not heretofore described in the literature.

$$R^{19}-NHCO-R^{18}-CONH-R^{20} \quad (4)$$

wherein $R^{18}$ means

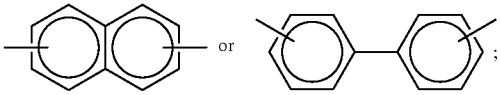

$R^{19}$ and $R^{20}$ may be the same or different and each means a $C_{5-12}$ cycloalkyl group.

These novel amide compounds can be produced basically by the conventional amidation reactions and particularly by the above-described processes (i), (ii) and (iii). Thus, any one of the following methods can be used, (a) A naphthalenedicarboxylic acid or biphenyldicarboxylic acid of the formula HOOC—$R^{18}$—COOH (hereinafter referred to as "dicarboxylic acid A") is reacted with 2 to 10 equivalents of a monoamine in an inert solvent at about 60 to 200° C. for about 2 to 8 hours.

In order to accelerate this reaction, said activator is preferably employed.

(b) Dichloride of said dicarboxylic acid A is reacted with 2 to 3 equivalents of a monoamine in an inert solvent at about 0–100° C. for about 1 to 5 hours.

(c) A di($C_{1-3}$) alkyl ester of dicarboxylic acid A is reacted with 2 to 20 equivalents of a monoamine in an inert solvent in the presence of an acid or basic catalyst, which is conventionally used in ester-amide interchange reactions as mentioned hereinbefore, and preferably in the presence of said basic catalyst, at about 0 to 150° C. for about 3 to 10 hours.

The inert solvent which is employed in the above processes (a), (b) and (c) may be identical with the inert solvent mentioned hereinbefore for processes (i), (ii) and (iii).

The monoamine for use in the above processes is the monoamine corresponding to the formula $R^{19}$—$NH_2$ or $R^{20}$—$NH_2$. Particularly preferred are $C_{5-12}$ cycloalkylamines such as cyclopentylamine, cyclohexylamine, cycloheptylamine, cyclooctylamine, cyclododecylamine and so on.

The compounds obtained by the above processes (i), (ii) and (iii) or processes (a), (b) and (c) can each be isolated and purified by the conventional procedures such as chromatography, reprecipitation, recrystallization, fractional crystallization, and so on.

Among the amide compounds of the formula (1), those which are more effective include N,N'-dicyclohexylterephthalamide, N,N'-dicyclohexyl-2,6-naphthalenedicarboxamide, N,N'-dicyclooctyl-2,6-naphthalenedicarboxamide, N,N'-dicyclohexyl-1,4-cyclohexanedicarboxamide, N,N'-dicyclohexyl-4,4'-biphenyldicarboxamide, N,N'-bis(p-methylphenyl)hexanediamide, N,N'-bis(p-ethylphenyl)hexanediamide, N,N'-bis(4-cyclohexylphenyl)hexanediamide, N,N'-diphenylhexanediamide, N,N'-diphenyloctanediamide and so on.

Among these, N,N'-dicyclohexylterephthalamide, N,N'-dicyclohexyl-2,6-naphthalenedicarboxamide and N,N'-dicyclohexyl-4,4'-biphenyldicarboxamide can provide higher proportion of β-crystal form under quenching condition.

Amide compounds of the formula (2)

The amide compound of the formula (2) can be easily produced by subjecting an alicyclic, heterocyclic or aromatic diamine of the formula:

$$NH_2-R^8-NH_2 \qquad (2a)$$

wherein $R^8$ is as defined hereinbefore and an alicyclic or aromatic monocarboxylic acid of the formula:

$$R^9-COOH \text{ or } R^{10}-COOH$$

to amidation reaction in the conventional manner.

This amidation reaction can be conducted in various conventional ways, but typically any one of the following processes may be mentioned.

(i') The above-mentioned diamine is reacted with the monocarboxylic acid in an inert solvent at about 60 to 200° C. for about 2 to 8 hours. The monocarboxylic acid is used generally in an amount of about 2 to 10 equivalents per one equivalent of the diamine. In this process, too, the activator mentioned for process (i) is preferably employed in order to accelerate the reaction. The activator is used generally in an equimolar amount with respect to the diamine.

(ii') The above diamine is reacted with the acid chloride of said monocarboxylic acid in an inert solvent at about 0 to 100° C. for about 1 to 5 hours. The monocarboxylic acid chloride is used generally in an amount of 2 to 3 equivalents per one equivalent of the diamine.

(iii') The above diamine is reacted with an ester, particularly a $C_{1-3}$ alkyl ester, of said monocarboxylic acid in an inert solvent in the presence of a catalyst at about 0 to 150° C. for about 3 to 10 hours. The monocarboxylic acid ester is generally used in an amount of about 2 to 20 equivalents per one equivalent of the diamine. The catalyst may be selected from among the acid and basic catalysts for conventional ester-amide interchange reactions as mentioned for said process (iii) and is preferably a basic catalyst.

When $R^9$ and $R^{10}$ in the formula (2) are dissimilar, a substantially equimolar mixture of 2 kinds of corresponding monocarboxylic acids (or a substantially equimolar mixture of 2 kinds of corresponding monocarboxylic acid chlorides or a substantially equimolar mixture of 2 kinds of corresponding monocarboxylic acid esters) is employed.

The inert solvent for use in said processes (i'), (ii') and (iii') can be the same as the solvent mentioned for processes (i), (ii) and (iii) for production of the compound of the formula (1).

The compound obtained by the above processes can be isolated and purified by the conventional procedures such as chromatography, reprecipitation, recrystallization, fractional crystallization and so on.

In the above processes (i'), (ii') and (iii'), the diamine of the formula (2a) is the alicyclic, heterocyclic or aromatic diamine corresponding to $R^8$. Thus, $R^8$ is preferably a residue formed by elimination of the two amino groups of one of the following alicyclic, heterocyclic and aromatic diamines.

Thus, the alicyclic diamine includes $C_{4-28}$, preferably $C_{6-15}$ alicyclic diamines such as 1,2-diaminocyclohexane, 1,4-diaminocyclohexane, 4,4'-diaminodicyclohexyl, 4,4'-diamino-3,3'-dimethyldicyclohexyl, 4,4'-diaminodicyclohexylmethane, 4,4'-diamino-3,3'-dimethyldicyclohexylmethane, 1,3-bis(aminomethyl)cyclohexane, 1,4-bis(aminomethyl)cyclohexane, and additionally includes isophoronediamine, menthenediamine and so on.

The heterocyclic diamine includes 5- or 6-membered heterocyclic diamines containing 1 or 2 nitrogen or sulfur atoms in the ring structure and having 4 to 14 carbon atoms, such as 2,3-diaminopyridine, 2,6-diaminopyridine, 3,4-diaminopyridine, o-tolidinesulfone and so on.

The aromatic diamine includes those containing 6 to 28, preferably 6 to 15 carbon atoms, such as o-phenylenediamine, m-phenylenediamine, p-phenylenediamine, 2,3-diaminotoluene, 2,4-diaminotoluene, 2,6-diaminotoluene, 3,4-diaminotoluene, 4,6-dimethyl-m-phenylenediamine, 2,5-dimethyl-p-phenylenediamine, 4,5-dimethyl-o-phenylenediamine, 2,4-diaminomesitylene, 1,5-diaminonaphthalene, 1,8-diaminonaphthalene, 2,3-diaminonaphthalene, 2,7-diaminonaphthalene, 9,10-diaminophenanthrene, 3,3',5,5'-tetramethylbenzidine, 3,3'-dimethyl-4,4'-diaminobiphenyl, 3,3'-dimethoxy-4,4'-diaminobiphenyl, 4,4'-diaminodiphenylmethane, 3,3'-diaminodiphenylmethane, 3,4'-diaminodiphenylmethane, 4,4'-methylenedi-o-toluidine, 4,4'-methylenedi-2,6-xylidine, 4,4'-methylenedi-2,6-diethylaniline, 4,4'-diamino-1,2-diphenylethane, 4,4'-diamino-2,2'-dimethylbibenzyl, 4,4'-diaminostilbene, 3,4'-diamino-2,2-diphenylpropane, 4,4'-diamino-2,2-diphenylpropane, 4,4,-diaminodiphenylether, 3,4'-diaminodiphenylether, 4,4'-thiodianiline, 2,2'-dithiodianiline, 4,4'-dithiodianiline, 3,3'-diaminodiphenylsulfone, 4,4'-diaminodiphenylsulfone, 3,3'-diaminobenzophenone, 4,4'-diaminobenzophenone, 4,4'-diaminobenzanilide, 2,7-diaminofluorene, 3,7-diamino-2-methoxyfluorene, bis-p-aminophenylaniline, 1,3-bis(4-aminophenylpropyl)benzene, 1,4-bis(4-aminophenylpropyl)benzene, 1,3-bis(4-aminophenoxy)benzene, 1,4-bis(4-aminophenoxy)benzene, 4,4'-bis(4-aminophenoxy)biphenyl, bis[4-(4-aminophenoxy)phenyl]ether, bis[4-(4-aminophenoxy)phenyl]sulfone, 9,9-bis(4-aminophenyl)fluorene and so on.

As preferred examples of the alicyclic monocarboxylic acid represented by $R^9$—COOH or $R^{10}$—COOH, there may be mentioned $C_4$–$C_{13}$ cycloalkanecarboxylic acids, $C_4$–$C_{13}$ cycloalkenecarboxylic acids,

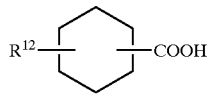

(wherein $R^{12}$ is as defined above),

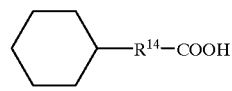

(wherein $R^{14}$ is as defined above), etc., and examples thereof are cyclopropanecarboxylic acid, cyclobutanecarboxylic acid, cyclopentanecarboxylic acid, 1-methylcyclopentanecarboxylic acid, 2-methylcyclopentane-carboxylic acid, 3-methylcyclopentanecarboxylic acid, 1-phenylcyclopentanecarboxylic acid, cyclopentenecarboxylic acid, cyclohexanecarboxylic acid, 1-methylcyclohexanecarboxylic acid,
2-methylcyclohexanecarboxylic acid,
3-methylcyclohexanecarboxylic acid,
4-methylcyclohexanecarboxylic acid,
4-propylcyclohexanecarboxylic acid,
4-butylcyclohexanecarboxylic acid,
4-pentylcyclohexanecarboxylic acid,
4-hexylcyclohexanecarboxylic acid,
4-phenylcyclohexanecarboxylic acid,
1-phenylcyclohexanecarboxylic acid, cyclohexenecarboxylic acid, 4-butylcyclohexenecarboxylic acid, cycloheptanecarboxylic acid, 1-cycloheptenecarboxylic acid, 1-methylcycloheptanecarboxylic acid, 4-methylcycloheptanecarboxylic acid, cyclohexylacetic acid and so on.

As preferred examples of the aromatic monocarboxylic acid represented by $R^9$—COOH or $R^{10}$—COOH, there may be mentioned

(wherein $R^{11}$ is as defined above),

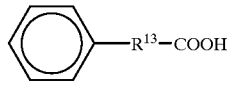

(wherein $R^{13}$ is as defined above), etc., and examples thereof are benzoic acid, o-methylbenzoic acid, m-methylbenzoic acid, p-methylbenzoic acid, p-ethylbenzoic acid, p-propylbenzoic acid, p-butylbenzoic acid, p-tert-butylbenzoic acid, p-pentylbenzoic acid, p-hexylbenzoic acid, o-phenylbenzoic acid, p-phenylbenzoic acid, p-cyclohexylbenzoic acid, phenylacetic acid, phenylpropionic acid, phenylbutyric acid and so on.

The more desirable species of the diamide compound of the formula (2) which can be obtained from said diamine and monocarboxylic acid include N,N'-1,4-phenylenebis-cyclohexanecarboxamide, N,N'-1,5-naphthalenebis-benzamide, N,N'-1,4-cyclohexanebis-benzamide, N,N'-1,4-cyclohexanebis-cyclohexanecarboxamide and so on.

It should be noted that the desired effect cannot be obtained when the amide compound of the formula (2) is a compound synthesized by using xylylenediamine as the aromatic diamine. Such compounds of the formula (2) wherein $R^8$ is —$CH_2$ —$C_6H_4$—$CH_2$—are excluded from the scope of the present invention.

Amide compounds of the formula (3)

The amide compound of the formula (3) can be easily prepared by subjecting an aliphatic, alicyclic or aromatic amino acid of the formula (3a)

$$NH_2—R^{15}—COOH \qquad (3a)$$

wherein $R^{15}$ is as defined hereinbefore, a monocarboxylic acid chloride of the formula $R^{16}$—COCl (wherein $R^{16}$ is as defined hereinbefore) and a monoamine of the formula $R^{17}$—$NH_2$ (wherein $R^{17}$ is as defined hereinbefore) to an amidation reaction.

This amidation reaction can be conducted, for example by reacting said amino acid of the formula (3a) with 1 to 2 equivalents of said monocarboxylic acid chloride in an inert solvent at about 0 to 100° C. for about 1 to 5 hours, then adding 1 to 5 equivalents, based on the reaction product, of said monoamine and conducting the reaction, preferably in the presence of the activator mentioned for process (i), at a temperature of about 60 to 200° C. for about 2 to 8 hours. The inert solvent may be any of the solvents mentioned hereinbefore in connection with process (i) for the production of said compound of the formula (1).

The compound obtained by the above process is purified by the conventional isolation and purification procedures such as chromatography, reprecipitation, recrystallization, fractional crystallization and so on.

The amino acid (3a) to be used in the above process is the aliphatic, alicyclic or aromatic amino acid corresponding to $R^{15}$. Thus, $R^{15}$ is preferably a residue formed by elimination of one amino group and one carboxyl group from one of the aliphatic, alicyclic and aromatic amino acids mentioned below.

As preferred examples of said aliphatic amino acid, there may be mentioned $C_{2-29}$, more preferably $C_{2-13}$, saturated or unsaturated aliphatic amino acids such as aminoacetic acid, α-aminopropionic acid, β-aminopropionic acid, α-aminoacrylic acid, α-aminobutyric acid, β-aminobutyric acid, γ-aminobutyric acid, α-amino-α-methylbutyric acid, γ-amino-α-methylenebutyric acid, α-aminoisobutyric acid, β-aminoisobutyric acid, α-amino-n-valeric acid, δ-amino-n-valeric acid, β-aminocrotonic acid, α-amino-β-methylvaleric acid, α-aminoisovaleric acid, 2-amino-4-pentenoic acid, α-amino-n-caproic acid, 6-aminocaproic acid, α-aminoisocaproic acid, 7-aminoheptanoic acid, α-amino-n-caprylic acid, 8-aminocaprylic acid, 9-aminononanoic acid, 11-aminoundecanoic acid, 12-aminododecanoic acid and so on.

The alicyclic amino acid includes $C_{7-13}$ saturated or unsaturated alicyclic amino acids such as
1-aminocyclohexanecarboxylic acid,
2-aminocyclohexanecarboxylic acid,
3-aminocyclohexanecarboxylic acid,
4-aminocyclohexanecarboxylic acid,
p-aminomethylcyclohexanecarboxylic acid, 2-amino-2-norbornanecarboxylic acid and so on.

The aromatic amino acid specifically includes $C_{7-15}$ aromatic amino acids such as α-aminophenylacetic acid, α-amino-β-phenylpropionic acid, 2-amino-2-phenylpropionic acid, 3-amino-3-phenylpropionic acid, α-aminocinnamic acid, 2-amino-4-phenylbutyric acid, 4-amino-3-phenylbutyric acid, anthranilic acid, m-aminobenzoic acid, p-aminobenzoic acid, 2-amino-4-methylbenzoic acid, 2-amino-6-methylbenzoic acid, 3-amino-4-methylbenzoic acid, 2-amino-3-methylbenzoic acid, 2-amino-5-methylbenzoic acid, 4-amino-2-methylbenzoic acid, 4-amino-3-methylbenzoic acid, 2-amino-3-methoxybenzoic acid, 3-amino-4-methoxybenzoic acid, 4-amino-2-methoxybenzoic acid, 4-amino-3-methoxybenzoic acid, 2-amino-4,5-dimethoxybenzoic acid, o-aminophenylacetic acid, m-aminophenylacetic acid, p-aminophenylacetic acid, 4-(4-aminophenyl)butyric acid, 4-aminomethylbenzoic acid, 4-aminomethylphenylacetic acid, o-aminocinnamic acid, m-aminocinnamic acid, p-aminocinnamic acid, p-aminohippuric acid, 2-amino-1-naphthoic acid, 3-amino-1-naphthoic acid, 4-amino-1-naphthoic acid, 5-amino-1-naphthoic acid, 6-amino-1-naphthoic acid, 7-amino-1-naphthoic acid, 8-amino-1-naphthoic acid, 1-amino-2-naphthoic acid, 3-amino-2-naphthoic acid, 4-amino-2-naphthoic acid, 5-amino-2-naphthoic acid, 6-amino-2-naphthoic acid, 7-amino-2-naphthoic acid, 8-amino-2-naphthoic acid and so on.

The monoamine ($R^{17}$—$NH_2$) as a starting compound for the amide compound of the formula (3) is identical with the monoamine ($R^2$—$NH_2$ or $R^3$—$NH_2$) used as a starting compound for the amide compound of the formula (1), and similarly the monocarboxylic acid chloride ($R^{16}COCl$) is one derived from the monocarboxylic acid which is identical with the monocarboxylic acid ($R^9COOH$ or $R^{10}COOH$) used as a starting compound for the amide compound of the formula (2).

Among various species of the amide compound of the formula (3), N-cyclohexyl-4-(N-cyclohexylcarbonylamino)-benzamide and N-phenyl-5-(N-benzoylamino)pentanamide, for instance, are particularly effective.

The β-nucleating agent of the formula (1), (2) or (3) can be added to polypropylene resin at an optional stage, i.e. either during the polymerization reaction or after the polymer has been prepared.

The amount of said β-nucleating agent to be added is not critical insofar as the desired effect can be obtained. Generally, it is used in an amount effective for increasing the content of the β-crystal form. Especially, based on 100 parts by weight of polypropylene resin, about 0.0001 to 5 parts by weight, preferably about 0.001 to 1 part by weight, of the β-nucleating agent is employed. If the proportion of the β-nucleating agent is less than 0.0001 part by weight, formation of the β-crystal form may not be sufficient, while the use of the β-nucleating agent in excess of 5 parts by weight may not be rewarded with a commensurate effect and be uneconomical.

Thus, the β-nucleating agent of the invention is capable of causing a crystalline polypropylene resin to undergo transition to the β-crystal form at a very low level of addition and a molded product having a I-form content of about 20 to 97%, particularly 40 to 97%, more preferably about 50 to 90% can be obtained under the conventional molding conditions.

The term 'polypropylene resin' as used in this specification and claim means not only a polypropylene homopolymer but also a polymer composed predominantly of propylene, particularly a polymer composed of not less than 50% by weight, preferably not less than 80% by weight, of propylene. As examples of the latter polymer, there may be mentioned propylene-ethylene random copolymer, propylene-ethylene block copolymer, polymer blends of said polypropylene resin with a small proportion of a thermoplastic resin, such as high-density polyethylene, polybutene-1, poly-4-methylpentene-1 or the like.

The catalyst which can be used for the production of such polymers includes not only Ziegler-Natta catalyst which is commonly employed but also a combination catalyst, such as one wherein a transition metal compound (e.g. titanium halides such as titanium trichloride, titanium tetrachloride, etc.) supported on a support composed mainly of magnesium halide, such as magnesium chloride, is combined with an alkylaluminum compound (e.g. triethylaluminum, diethylaluminum chloride, etc.).

The melt flow rate (hereinafter referred to briefly as "MFR"; measured in accordance with JIS K 6758-1981) of the crystalline polypropylene resin can be appropriately selected according to the molding method to be employed and is generally about 0.1 to 100 g/10 min. and preferably about 0.5 to 50 g/10 min.

If required, the resin composition of the present invention may contain a variety of additives such as a stabilizer (e.g. epoxy compounds), an antioxidant (e.g. phenol compounds, phosphite compounds), an ultraviolet absorber (benzophenone compounds, benzotriazole compounds), a neutralizer, a nucleating agent, an antistatic agent, an antiblocking agent, a lubricant (e.g. aliphatic hydrocarbons, higher fatty acids, and the alkali metal salts or alkaline earth metal salts thereof, fatty acid esters, higher fatty acid amides, rosin derivatives), a colorant, an elastomer, and a mineral (e.g. talc, hydrotalcite), each within a range not interfering with the effect of the invention.

The crystalline polypropylene resin composition of the invention is preferably produced by mixing said β-nucleating agent and polypropylene resin, with or without addition of said additives, in an ordinary mixer, such as a Henschel mixer, and if necessary, pelletizing the resulting mixture using an ordinary pelletizer, such as a single-screw extruder, in the per se known manner.

The resulting crystalline polypropylene resin composition of the invention can be molded by various known techniques. Thus, injection molding, extrusion molding, compression molding and other molding techniques utilizing the conventional molding machines can be employed. Molding conditions may be those commonly employed. Typical preferred molding conditions may be as follows. Injection molding: resin temperature about 200 to 300° C., preferably about 240 to 280° C.; mold temperature about 30 to 120° C., preferably about 50 to 80° C. Extrusion molding: resin temperature about 200 to 300° C., preferably about 240 to 280° C.; chill roll temperature about 40 to 140° C., preferably about 60 to 120° C. Compression molding: temperature of melted resin about 200 to 300° C., preferably about 240 to 280° C.; cooling temperature about 30 to 120° C., preferably about 50 to 100° C.

Molded product, which contains much higher proportion of β-crystal form than before and which is satisfactory in the aspect of color, can be easily obtained by molding under the above-mentioned molding condition the resin composition of the invention prepared with use of the above-mentioned mixing method. Compared with the conventional polypropylene pellet which does not substantially contain β-crystals but is predominantly composed of α-crystals, the polypropylene molded product has lower melting point and requires a less force for deformation under heating. Therefore, the molded products contributes a great deal to improved secondary processability and mechanical characteristics. The products encompass a wide variety of forms such as packages, sheet, film and so on.

With the resin composition of the present invention, the ratio of α- to β-forms in the final product can be controlled as desired by suitably selecting molding conditions such as cooling conditions. For example, the proportion of R-form is increased as a higher cooling temperature is employed. Thus, it is possible to control the ratio of α- to β-forms by appropriately selecting cooling condition under the above molding condition. This characteristic is beneficial particularly in the surface roughening of biaxially oriented film. The film having such a roughened surface displays excellent antiblocking property, printability and adhesion, etc. and is of great use in the fields of packaging film, printing paper, tracing paper, oil-immersion type plastic capacitors and so on.

Moreover, the resin composition containing a naphthalenedicarboxylic acid di($C_{3-12}$)cycloalkylamide, which is among the amide compounds of the invention, is extremely useful for improving the impact strength of moldings and can exhibit excellent utility in a variety of applications such as automotive and electrical parts, etc.

EXAMPLES

The following examples and comparative examples are intended to describe the invention in further detail. In these examples and comparative examples, the β-form content, modulus in flexure and impact strength were determined by the following methods.

(1) Determination of β-form content

A sample (5–10 mg), cut from the sheet obtained in each Example and Comparative Example by punching, is set in the sample holder of a differential scanning calorimeter (DSC) and melted by heating in a nitrogen gas atmosphere at 230° C. for 5 minutes. The temperature is then decreased at a rate of 20° C./min to near room temperature and, then, increased again at a rate of 20° C./min. From the peak areas of the α- and β-crystal forms on the DSC thermogram thus obtained, the β-form content (area %) is calculated by means of the following equation.

$$\beta\text{-form content } (\%) = 100 \times A_\beta / (A_\alpha + A_\beta)$$

where $A_{\alpha}$ means the peak area of α-form and $A_\beta$ means the peak area of β-form.

(2) Determination of modulus in flexure

The modulus was determined in accordance with JIS K 7203. The testing temperature was 25° C. and the testing speed was 10 mm/min.

(3) Impact strength (duPont method)

In accordance with the falling weight impact test method described in JIS K 7211, the 50% destruction energy for a 2 mm-thick sheet at 23° C. was determined.

Example 1

To 100 parts by weight of a propylene homopolymer powder (MFR=14 g/10 min) was added 0.05 part by weight of N,N'-dicyclohexylterephthalamide and the mixture was milled in a Henschel mixer and pelletized with a 20 mm-diameter single-screw extruder. The resulting pellets were subjected to compression-molding by melting the pellets at 230° C. for 10 minutes and then placing it in a mold of 60° C. and maintaining it therein for 5 minutes for solidification to give a 0.5 mm-thick sheet. The β-form content of the resulting sheet was 93% and the sheet showed no coloration.

Example 2

Except that N,N'-dicyclohexyl-1,4-cyclohexanedicarboxamide was used as the β-nucleating agent, the procedure of Example 1 was otherwise repeated to provide a sheet. The β-form content of this sheet was 42% and the sheet showed no coloration.

Example 3

Except that N,N'-dicylohexyl-2,6-naphthalenedicarboxamide was used as the β-nucleating agent, the procedure of Example 1 was repeated to provide a sheet. The β-form content of this sheet was 97% and the sheet showed no coloration.

Example 4

Except that N,N'-dicylohexyl-4,4'-biphenyldicarboxamide was used as the β-nucleating agent, the procedure of Example 1 was repeated to provide a sheet. The β-form content of this sheet was 59% and the sheet showed no coloration.

Example 5

Except that N,N'-bis(p-methylphenyl)hexanediamide was used as the β-nucleating agent, the procedure of Example 1 was repeated to provide a sheet. The β-form content of this sheet was 89% and the sheet showed no coloration.

Example 6

Except that N,N'-bis(p-ethylphenyl)hexanediamide was used as the β-nucleating agent, the procedure of Example 1 was repeated to provide a sheet. The β-form content of this sheet was 64% and the sheet showed no coloration.

Example 7

Except that N,N'-bis (4-cyclohexylphenyl)hexanediamide was used as the β-nucleating agent, the procedure of Example 1 was repeated to provide a sheet. The β-form content of this sheet was 82% and the sheet showed no coloration.

Example 8

Except that 0.05 part by weight of N,N'-1,4-phenylenebis-cyclohexanecarboxamide was used as the β-nucleating agent, the procedure of Example 1 was repeated to provide a sheet. The β-form content of this sheet was 84% and the sheet showed no coloration.

Example 9

Except that N,N'-1,5-naphthalenebis-benzamide was used as the β-nucleating agent, the procedure of Example 1 was repeated to provide a sheet. The β-form content of this sheet was 44% and the sheet showed no coloration.

Example 10

Except that N,N'-1,4-cyclohexanebis-benzamide was used as the β-nucleating agent, the procedure of Example 1 was repeated to provide a sheet. The β-form content of this sheet was 92% and the sheet showed no coloration.

Example 11

Except that N,N'-1,4-cyclohexanebis-cyclohexanecarboxamide was used as the β-nucleating agent, the procedure of Example 1 was repeated to provide a sheet. The β-form content of this sheet was 85% and the sheet showed no coloration.

Example 12

Except that N-cyclohexyl-4-(N-cyclohexylcarbonylamino)benzamide was used as the β-nucleating agent, the procedure of Example 1 was repeated to provide a sheet. The β-form content of this sheet was 42% and the sheet showed no coloration.

Example 13

Except that N-phenyl-5-(N-benzoylamino)pentanamide was used as the β-nucleating agent, the procedure of Example 1 was repeated to provide a sheet. The β-form content of this sheet was 38% and the sheet showed no coloration.

Example 14

Except that polypropylene homopolymer (MFR=4.3 g/10 min) was used as the polypropylene, the procedure of Example 1 was repeated to provide a sheet. The β-form content of this sheet was 95% and the sheet showed no coloration.

Comparative Example 1

Except that N,N'-dicyclohexylterephthalamide was not added, the procedure of Example 1 was repeated to provide a sheet and its β-form content was determined. This sheet contained only a trace amount of β-form. The sheet showed no coloration.

Comparative Example 2

Except that γ-quinacridone was used as the β-nucleating agent, the procedure of Example 1 was repeated to provide a sheet. However, under the particular conditions used, the sheet contained only a trace amount of β-form. The sheet had a red color.

Example 15

To 100 parts by weight of a propylene homopolymer powder (MFR=14 g/10 min) was added 0.2 part by weight of N,N'-dicyclohexyl-2,6-naphthalenedicarboxamide and the mixture was milled in a Henschel mixer and pelletized with a 20 mm-diameter single-screw extruder. The resulting pellets were injection-molded at a resin temperature of 240° C. and a mold temperature of 50° C. to provide a test piece. The modulus in flexure of the above test piece was 151 kgf/mm$^2$. The duPont impact strength was 41 kgf·cm.

Comparative Example 3

Except that N,N'-dicyclohexyl-2,6-naphthalenedicarboxamide was not added, the procedure of Example 15 was otherwise repeated to provide a sheet. This sheet had a modulus in flexure of 139 kgf/mm2 and a duPont impact strength of 3 kgf·cm.

Example 16

A 300 ml four-necked flask equipped with a stirrer, thermometer, condenser and gas inlet was charged with 6.48 g (0.03 mole) of 2,6-naphthalenedicarboxylic acid, 5.61 g (0.066 mole) of cyclopentylamine, 20.46 g (0.066 mol) of triphenyl phosphite, 25 g of pyridine and 100 g of N-methylpyrrolidone, and the reaction was carried out in a nitrogen gas atmosphere at 100° C. for 3 hours, with stirring. After cooling, the reaction mixture was poured in 700 ml of isopropyl alcohol/water (1:1) for reprecipitation and washing. The mixture was stirred for 2 hours and the precipitate was then recovered by filtration and dried under reduced pressure at 110° C. to provide 9.03 g (yield 86%) of N,N'-dicyclopentyl-2,6-naphthalenedicarboxamide. This compound was a white powder melting at 375.4° C. (decomp.). The elemental analysis and characteristic infrared absorptions are shown in Table 1.

Example 17

Except that 6.53 g (0.066 mole) of cyclohexylamine was used as the monoamine, the procedure of Example 16 was otherwise repeated to provide 9.64 g (yield 85%) of N,N'-dicyclohexyl-2,6-naphthalenedicarboxamide. This compound was a white powder melting at 384.2° C. (decomp.). The elemental analysis and characteristic infrared absorptions are shown in Table 1.

Except that the above compound was used as the β-nucleating agent, the procedure of Example 1 was otherwise repeated to provide a sheet. The β-form content of this sheet was 97% and the sheet showed no coloration.

Example 18

Except that 8.38 g (0.066 mole) of cyclooctylamine was used as the monoamine, the procedure of Example 16 was otherwise repeated to provide 9.63 g (yield 74%) of N,N'-dicyclooctyl-2,6-naphthalenedicarboxamide. This compound was a white powder melting at 320.8° C. (decomp.). The elemental analysis and characteristic infrared absorptions are shown in Table 1.

Example 19

Except that 12.08 g (0.066 mole) of cyclododecylamine was used as the monoamine, the procedure of Example 16 was repeated to provide 13.3 g (yield 81%) of N,N'-dicyclododecyl-2,6-naphthalenedicarboxamide. This compound was a white powder melting at 321.8° C. (decomp.). The elemental analysis and characteristic infrared absorptions are shown in Table 1.

Example 20

Except that 6.48 g (0.03 mole) of 2,7-naphthalenedicarobxylic acid was used as the dicarboxylic acid, the procedure of Example 17 was otherwise repeated to provide 8.39 g (yield 74%) of N,N'-dicyclohexyl-2,7-naphthalenedicarboxamide. This compound was a white powder melting at 337.1° C. (decomp.). The elemental analysis and characteristic infrared absorptions are shown in Table 1.

Example 21

Except that 7.26 g (0.03 mole) of 4,4'-biphenyldicarboxylic acid was used as the dicarboxylic acid, the procedure of Example 16 was otherwise repeated to provide 8.12 g (yield 72%) of N,N'-dicyclopentyl-4,4'-biphenyldicarboxamide. This compound was a white powder melting at 355.0° C. (decomp.). The elemental analysis and characteristic infrared absorptions are shown in Table 1.

Example 22

Except that 6.53 g (0.066 mole) of cyclohexylamine was used as the monoamine, the procedure of Example 21 was otherwise repeated to provide 9.94 g (yield 82%) of N,N'-dicyclohexyl-4,4'-biphenyldicarboxamide. This compound was a white powder melting at 370.8° C. (decomp.). The elemental analysis and characteristic infrared absorptions are shown in Table 1.

Except that the above compound was used as the β-nucleating agent, the procedure of Example 1 was otherwise repeated to provide a sheet. The β-form content of this sheet was 59% and the sheet showed no coloration.

Example 23

Except that 8.38 g (0.066 mole) of cyclooctylamine was used as the monoamine, the procedure of Example 21 was otherwise repeated to provide 10.8 g (yield 78%) of N,N'-dicyclooctyl-4,4'-biphenyldicarboxamide. This compound was a white powder melting at 320.2° C. (decomp.). The elemental analysis and characteristic infrared absorptions are shown in Table 1.

Example 24

Except that 12.08 g (0.066 mole) of cyclododecylamine was used as the monoamine, the procedure of Example 21 was otherwise repeated to provide 17.16 g (yield 82%) of N,N'-dicyclododecyl-4,4'-biphenyldicarboxamide. This compound was a white powder melting at 346.7° C. (decomp.). The elemental analysis and characteristic infrared absorptions are shown in Table 1.

Example 25

A reactor was charged with 8.37 g (0.03 mole) of 2,2'-biphenyldicarboxylic acid dichloride, 11.88 g (0.12 mole) of cyclohexylamine and 120 g of chlorobenzene and the reaction was carried out in a nitrogen gas atmosphere at 80° Cc for 2.5 hours. After cooling, the reaction mixture was poured in 1000 ml of hexane for reprecipitation and washing. The precipitate was washed with 600 ml of a 0.5% aqueous sodium hydroxide solution and further with purified water thoroughly. The precipitate was collected by filtration and dried under reduced pressure at 110° C. to provide 6.08 g (yield 50%) of N,N'-dicycohexyl-2,2'-biphenyldicarboxamide. This compound was a white powder melting at 229.2–229.8° C. The elemental analysis and characteristic infrared absorptions are shown in Table 1.

TABLE 1

| Example | Elemental Analysis (%) Calcd. | Elemental Analysis (%) Found | Infrared spectra (cm$^{-1}$) |
|---|---|---|---|
| 16 | C: 75.40 | C: 75.28 | 1330, 1553, 1628, 3264 (amido) |
|  | H: 7.48 | H: 7.61 | 1450, 2869, 2960 (cyclopentyl) |
|  | N: 7.99 | N: 7.84 | 697, 774, 838, 1595, 3074 (2,6-naphthalene) |
| 17 | C: 76.16 | C: 76.04 | 1320, 1537, 1631, 3306 (amido) |
|  | H: 7.99 | H: 8.12 | 1450, 2853, 2937 (cyclohexyl) |
|  | N: 7.40 | N: 7.28 | 697, 778, 820, 1605, 3063 (2,6-naphthalene) |
| 18 | C: 77.38 | C: 77.29 | 1315, 1529, 1632, 3317 (amido) |
|  | H: 8.81 | H: 8.88 | 1448, 2860, 2924 (cyclooctyl) |
|  | N: 6.45 | N: 6.37 | 697, 775, 819, 1605, 3062 (2,6-naphthalene) |

TABLE 1-continued

| Example | Elemental Analysis (%) Calcd. | Elemental Analysis (%) Found | Infrared spectra (cm$^{-1}$) |
|---|---|---|---|
| 19 | C: 79.07 | C: 78.89 | 1327, 1536, 1634, 3317 (amido) |
|  | H: 9.95 | H: 10.16 | 1469, 2862, 2944 (cyclododecyl) |
|  | N: 5.12 | N: 4.96 | 698, 768, 825, 1598, 3064 (2,6-naphthalene) |
| 20 | C: 76.16 | C: 76.02 | 1338, 1565, 1640, 3241 (amido) |
|  | H: 7.99 | H: 8.10 | 1454, 2852, 2929 (cyclohexyl) |
|  | N: 7.40 | N: 7.28 | 729, 822, 855, 1620, 3068 (2,7-naphthalene) |
| 21 | C: 76.56 | C: 76.38 | 1324, 1532, 1630, 3307 (amido) |
|  | H: 7.50 | H: 7.70 | 1451, 2869, 2957 (cyclopentyl) |
|  | N: 7.44 | N: 7.32 | 760, 843, 1492 (4,4'-biphenyl) |
| 22 | C: 77.19 | C: 77.03 | 1328, 1529, 1632, 3319 (amido) |
|  | H: 7.97 | H: 8.13 | 1449, 2854, 2936 (cyclohexyl) |
|  | N: 6.92 | N: 6.77 | 759, 843, 1491 (4,4'-biphenyl) |
| 23 | C: 78.22 | C: 78.40 | 1327, 1532, 1626, 3314 (amido) |
|  | H: 8.75 | H: 8.91 | 2847, 2926 (cyclooctyl) |
|  | N: 6.08 | N: 5.92 | 758, 840, 1493 (4,4'-biphenyl) |
| 24 | C: 79.67 | C: 79.41 | 1329, 1538, 1636, 3324 (amido) |
|  | H: 9.85 | H: 10.00 | 1444, 2863, 2947 (cyclododecyl) |
|  | N: 4.89 | N: 4.69 | 757, 841, 1492 (4,4'-biphenyl) |
| 25 | C: 77.19 | C: 77.08 | 1339, 1558, 1635, 3241 (amido) |
|  | H: 7.97 | H: 8.06 | 1450, 2854, 2931 (cyclohexyl) |
|  | N: 6.92 | N: 6.84 | 758, 1471 (2,2'-biphenyl) |

Table 2 below shows the structure each of the β-nucleating agents used in Examples 1–25.

TABLE 2

| Example | Structure |
|---|---|
| 1 | Cyclohexyl—NHCO—(phenylene)—CONH—Cyclohexyl |
| 2 | Cyclohexyl—NHCO—(cyclohexylene)—CONH—Cyclohexyl |
| 3 | Cyclohexyl—NHCO—(2,6-naphthylene)—CONH—Cyclohexyl |
| 4 | Cyclohexyl—NHCO—(4,4'-biphenylene)—CONH—Cyclohexyl |
| 5 | H$_3$C—(phenylene)—NHCO—(CH$_2$)$_4$—CONH—(phenylene)—CH$_3$ |
| 6 | H$_5$C$_2$—(phenylene)—NHCO—(CH$_2$)$_4$—CONH—(phenylene)—C$_2$H$_5$ |

TABLE 2-continued
| Example | Structure |
| --- | --- |
| 7 | 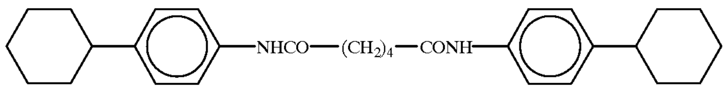 |
| 8 | 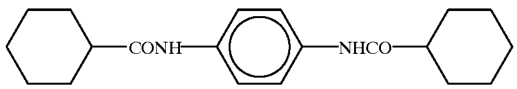 |
| 9 | 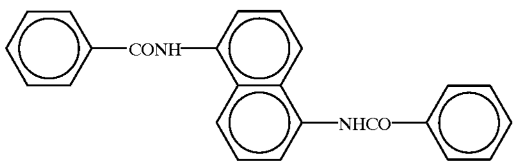 |
| 10 | 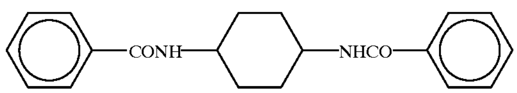 |
| 11 | 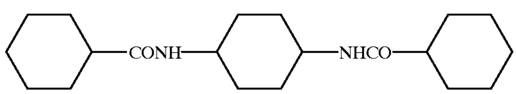 |
| 12 | 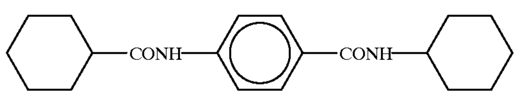 |
| 13 | 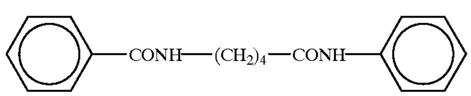 |
| 14 | 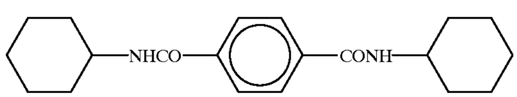 |
| 15 | 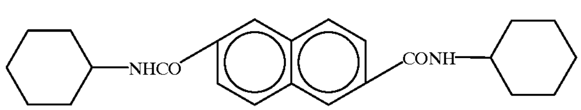 |
| 16 | 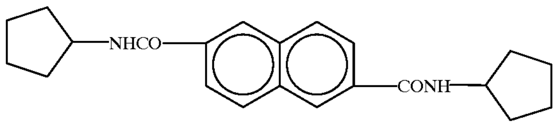 |
| 17 | 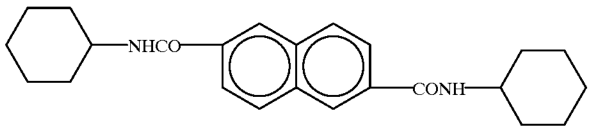 |
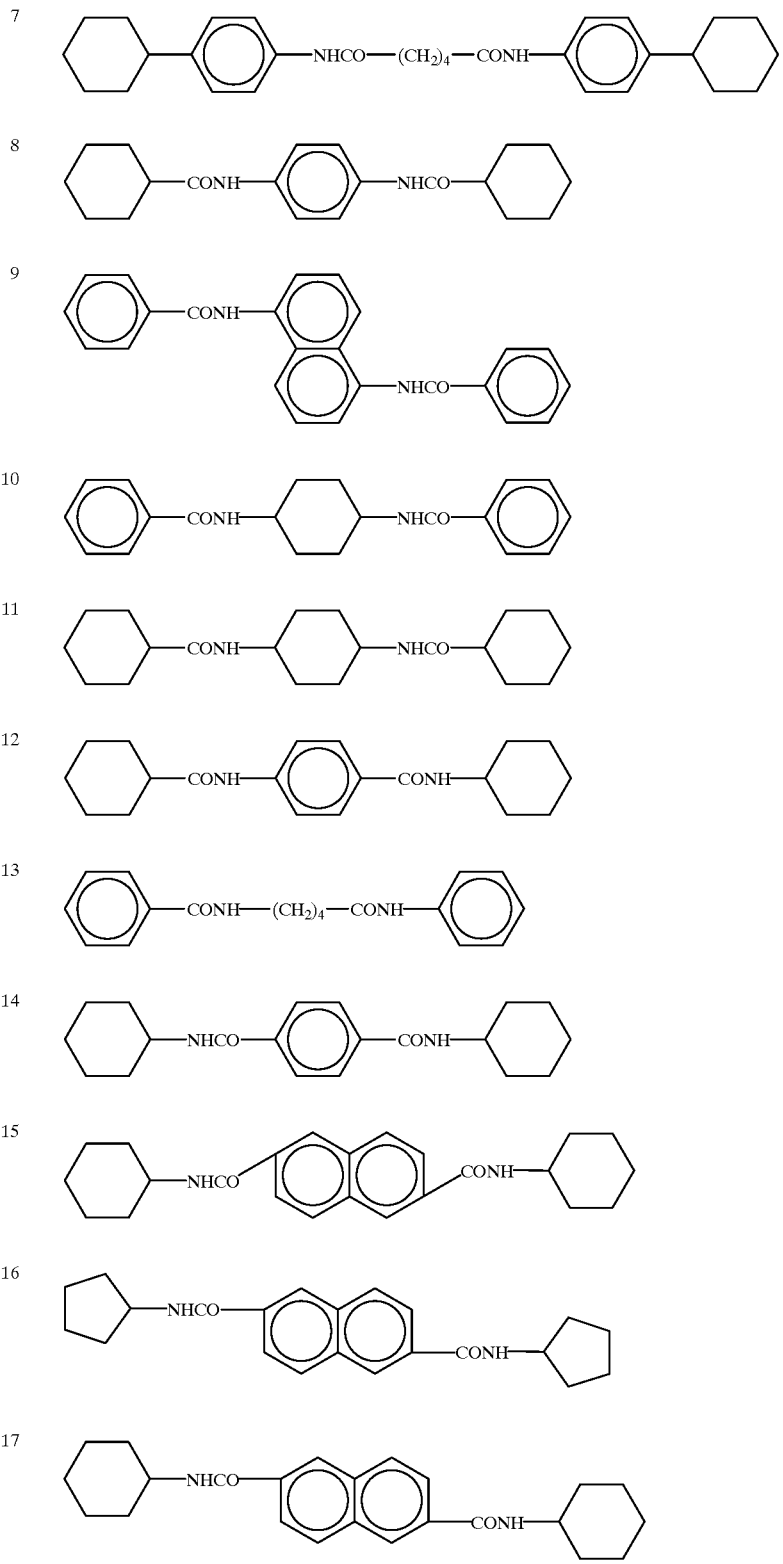

TABLE 2-continued

| Example | Structure |
|---|---|
| 18 | 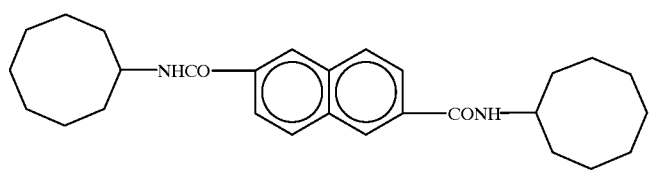 |
| 19 | 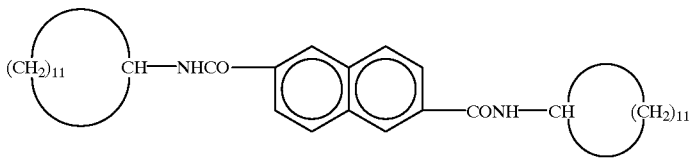 |
| 20 | 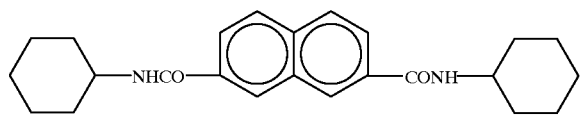 |
| 21 | 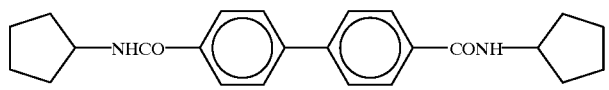 |
| 22 | 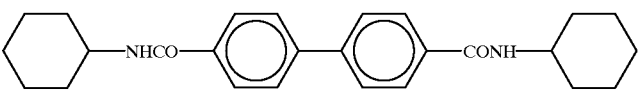 |
| 23 | 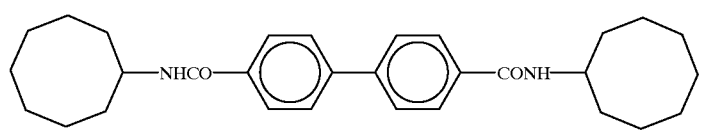 |
| 24 | 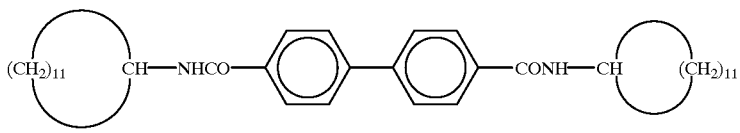 |
| 25 | 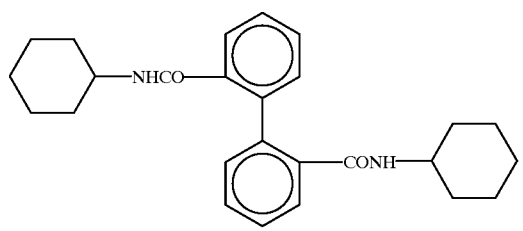 |

Examples 26 and 27

Except that N,N'-diphenylhexanediamide (Example 26) or N,N'-diphenyloctanediamide (Example 27) was used as the β-nucleating agent, the procedure of Example 1 was repeated to provide a sheet. The β-form contents of the resulting sheets are shown in Table 3 below.

Comparative Examples 3–8

Except that each of the amide compounds listed in Table 3 below (i.e., N,N'-diphenyl-butanediamide; N,N'-diphenylpentanediamide, N,N'-diphenyl-heptanediamide, N,N'-diphenyl-nonanediamide, N,N'-diphenyl-decanediamide and N,N'-diphenyl-terephthalamide) was used as the β-nucleating agent, the procedure of Example 1 was repeated to provide a sheet. The Inform contents of the resulting sheets are shown in Table 3 below.

TABLE 3

| | Structure | β-form content (%) |
|---|---|---|
| Example 26 | ⬡—NHCO—(CH₂)₄—CONH—⬡ | 91 |
| Example 27 | ⬡—NHCO—(CH₂)₆—CONH—⬡ | 83 |
| Comparative Example 3 | ⬡—NHCO—(CH₂)₂—CONH—⬡ | 9 |
| Comparative Example 4 | ⬡—NHCO—(CH₂)₃—CONH—⬡ | 3 |
| Comparative Example 5 | ⬡—NHCO—(CH₂)₅—CONH—⬡ | 5 |
| Comparative Example 6 | ⬡—NHCO—(CH₂)₇—CONH—⬡ | trace |
| Comparative Example 7 | ⬡—NHCO—(CH₂)₈—CONH—⬡ | trace |
| Comparative Example 8 | ⬡—NHCO—⬡—CONH—⬡ | trace |

What is claimed is:

1. A crystalline polypropylene resin composition consisting essentially of a crystalline polypropylene resin and a β-nucleating agent, said β-nucleating agent being present in the composition in an amount effective for providing an increased proportion of β-form crystals, and said β-nucleating agent being at least one member selected from the group consisting of:

(1) an amide compound of the formula:

$$R^2\text{—NHCO—}R^1\text{—CONH—}R^3 \quad (1)$$

wherein $R^1$ represents a residue formed by elimination of the two carboxyl groups of a $C_{3-20}$ saturated or unsaturated aliphatic dicarboxylic acid, a $C_{6-30}$ saturated or unsaturated alicyclic dicarboxylic acid or a $C_{8-30}$ aromatic dicarboxylic acid; $R^2$ and $R^3$ are the same or different and each represents a $C_{3-12}$ cycloalkyl group, a $C_{3-12}$ cycloalkenyl group, or a group of the formula:

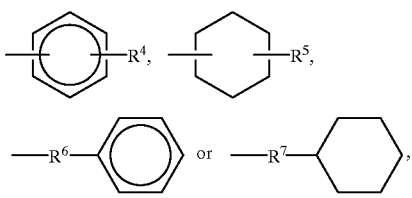

wherein $R^4$ represents a hydrogen atom, a $C_{1-2}$ straight- or branched-chain alkyl group, a $C_{2-12}$ straight- or branched-chain alkenyl group, a $C_{6-10}$ cycloalkyl group or a phenyl group; $R^5$ represents a $C_{1-12}$ straight- or branched-chain alkenyl group, a $C_{2-12}$ straight- or branched-chain alkenyl group, a $C_{6-10}$ cycloalkyl group or a phenyl group; and $R^6$ and $R^7$ each represents a $C_{1-4}$ straight-or branched-chain alkylene group; with the proviso that when $R^4$ is a hydrogen atom, a $C_{1-12}$ alkyl group or a $C_{6-10}$ cycloalkyl group, $R^1$ is a residue formed by the elimination of the two carboxyl group of a $C_6$ or $C_8$ saturated aliphatic dicarboxylic acid, (2) an amide compound of the formula:

$$R^9\text{—CONH—}R^8\text{—NHCO—}R^{10} \qquad (2)$$

wherein $R^8$ represents a residue formed by elimination of the two amino groups of a $C_{4-28}$ alicyclic diamine, a $C_{4-14}$ 5- or 6- membered heterocyclic diamine containing 1 or 2 nitrogen or sulfur atoms in its ring or a $C_{6-28}$ aromatic diamine; $R^9$ and $R^{10}$ are the same or different and each represents a $C_{3-12}$ cycloalkyl group, a $C_{3-12}$ cycloalkenyl group, or a group of the formula:

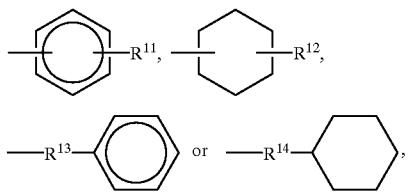

wherein $R^{11}$ represents a hydrogen atom, a $C_{1-12}$ straight- or branched-chain alkyl group, a $C_{2-12}$ straight- or branched-chain alkyl group, a $C_{6-10}$ cycloalkyl group or a phenyl group; $R^{12}$ represents a $C_{1-12}$ straight- or branched-chain alkyl group, a $C_{2-12}$ alkenyl group, a $C_{6-10}$ cycloalkyl group or a phenyl group; $R^{13}$ and $R^{14}$ each represents a $C_{1-4}$ straight- or branched-chain alkylene group; with the proviso that $R^8$ is not:

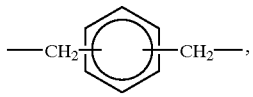

and (3) an amide compound of the formula:

$$R^{16}\text{—CONH—}R^{15}\text{—CONH—}R^{17} \qquad (3)$$

wherein $R^{15}$ represents a residue formed by elimination of one amino group and one carboxyl group of a $C_{2-29}$ saturated or unsaturated aliphatic amino acid, a $C_{7-13}$ saturated or unsaturated alicyclic amino acid or a $C_{7-15}$ aromatic amino acid; and $R^{16}$ and $R^{17}$ are the same or different and $R^{16}$ has the same meaning as $R^9$ or $R^{10}$ in the formula (2) and $R^{17}$ has the same meaning as $R^2$ or $R^3$ in the formula (1).

2. The composition as claimed in claim 1 wherein the β-nucleating agent is an amide compound of the formula (1).

3. The composition as claimed in claim 2 wherein the β-nucleating agent is an amide compound of the formula (1) wherein $R^1$ is —$(CH_2)_4$—,

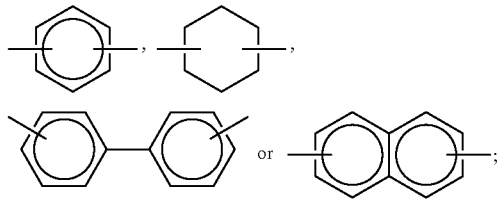

$R^2$ and $R^3$ are the same or different and each represents a $C_{6-8}$ cycloalkyl group or represents a phenyl group substituted by a $C_{1-4}$ alkyl or cyclohexyl group.

4. The composition as claimed in claim 2 wherein the β-nucleating agent is at least one amide compound selected from the group consisting of N,N'-dicyclohexylterephthalamide, N,N'-dicyclohexyl-2,6-naphthalenedicarboxamide, N,N'-dicyclooctyl-2,6-naphthalenedicarboxamide, N,N'-dicyclohexyl-1,4-cyclohexanedicarboxamide, N,N'-dicyclohexyl-4,4'-biphenyldicarboxamide, N,N'-bis(p-methylphenyl4)hexanediamide, N,N'-bis(p-ethylphenyl)hexanediamide, N,N'-bis(4-cyclohexylphenyl)hexanediamide, N,N'-diphenyl-hexanediamide and N,N'-diphenyl-octanediamide.

5. The composition as claimed in claim 2 wherein the β-nucleating agent is at least one amide compound selected from the group consisting of N,N'-dicyclohexyl-terephthalamide, N,N'-dicyclohexyl-2,6-naphthalenedicarboxamide and N,N'-dicyclohexyl-4,4'-biphenyldicarboxamide.

6. The composition as claimed in claim 1 wherein the β-nucleating agent is an amide compound of the formula (2).

7. The composition as claimed in claim 6 wherein the β-nucleating agent is an amide compound of the formula (2) wherein $R^8$ is

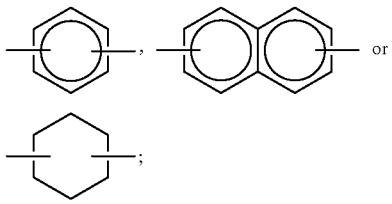

$R^9$ and $R^{10}$ are the same or different and each is a cyclohexyl group or a phenyl group.

8. The composition as claimed in claim 6 wherein the β-nucleating agent is at least one compound selected from the group consisting of N,N'-1,4-phenylenebis-cyclohexanecarboxamide, N,N'-1,5-naphthalenebis-benzamide, N,N'-1,4-cyclohexanebis-benzamide and N,N'-1,4-cyclohexanebis-cyclohexanecarboxamide.

9. The composition as claimed in claim 1 wherein the β-nucleating agent is an amide compound of the formula (3).

10. The composition as claimed in claim 9 wherein the β-nucleating agent is at least one compound selected from the group consisting of N-cyclohexyl-4-(N-cyclohexylcarbonylamino)-benzamide and N-phenyl-5-(N-benzoylamino)-pentanamide.

11. The method as claimed in claim 10 wherein the β-nucleating agent is an amide compound of the formula (1).

12. The method as claimed in claim 11 wherein the β-nucleating agent is an amide compound of the formula (1) wherein $R^1$ is —$(CH_2)_4$—,

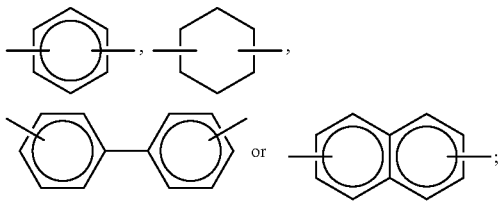

and $R^2$ and $R^3$ are the same or different and each represents a $C_{6-8}$ cycloalkyl group or represents a phenyl group substituted by a $C_{1-4}$ alkyl or cyclohexyl group.

13. The method as claimed in claim 11 wherein the β-nucleating agent is at least one amide compound selected from the group consisting of N,N'-dicyclohexylterephthalamide, N,N'-dicyclohexyl-2,6-naphthalenedicarboxamide, N,N'-dicyclooctyl-2,6-naphthalenedicarboxamide, N,N'-dicyclohexyl-1,4-cyclohexanedicarboxamide, N,N'-dicyclohexyl-4,4'-biphenyldicarboxamide, N,N'-bis(p-methylphenyl)hexanediamide, N,N'-bis(p-ethylphenyl)hexanediamide, N,N'-bis(4-cyclohexylphenyl)hexanediamide, N,N'-diphenylhexanediamide and N,N'-diphenyloctanediamide.

14. The method as claimed in claim 11 wherein the β-nucleating agent is at least one amide compound selected from the group consisting of N,N'-dicyclohexylterephthalamide, N,N'-dicyclohexyl-2,6-naphthalenedicarboxamide and N,N'-dicyclohexyl-4,4'-biphenyldicarboxamide.

15. The method as claimed in claim 11 wherein the β-nucleating agent is an amide compound of the formula (2).

16. The method as claimed in claim 15 wherein the β-nucleating agent is an amide compound of the formula (2) wherein $R^8$ is

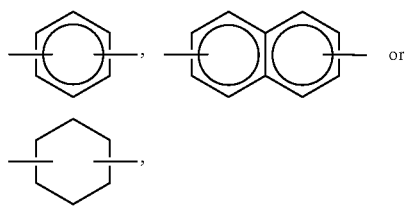

$R^9$ and $R^{10}$ are the same or different and each is a cyclohexyl group or a phenyl group.

17. The method as claimed in claim 15 wherein the β-nucleating agent is at least one compound selected from the group consisting of N,N'-1,4-phenylenebis-cyclohexanecarboxamide, N,N'-1,5-naphthalenebis-benzamide, N,N'1,4-cyclohexanebis-benzamide and N,N'-1,4-cyclohexanebis-cyclohexanecarboxamide.

18. The method as claimed in claim 12 wherein the β-nucleating agent is an amide compound of the formula (3).

19. The method as claimed in claim 18 wherein the β-nucleating agent is at least one compound selected from the group consisting of N-cyclohexyl-4-(N-cyclohexylcarbonylamino)-benzamide and N-phenyl-5-(N-benzoylamino)-pentanamide.

20. A novel amide compound of the the formula:

wherein $R^{18}$ represent

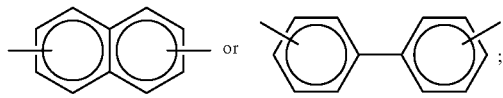

and $R^{19}$ and $R^{20}$ are the same or different and each represents a cycloalkyl group of 5 to 12 carbon atoms.

21. A method of increasing the proportion of β-form crystals in a crystalline polypropylene resin molded product which comprises molding a crystalline polypropylene resin composition consisting essentially of a crystalline polypropylene resin and at least one β-nucleating agent selected from the group consisting of (1) an amide compound of the formula:

wherein $R^1$ represents a residue formed by elimination of the two carboxyl groups of a $C_{3-20}$ saturated or unsaturated aliphatic dicarboxylic acid, a $C_{6-30}$ saturated or unsaturated alicyclic dicarboxylic acid or a $C_{8-30}$ aromatic dicarboxylic acid; $R^2$ and $R^3$ are the same or different and each represents a $C_{3-12}$ cycloalkyl group, a $C_{3-12}$ cycloalkenyl group, or a group of the formula:

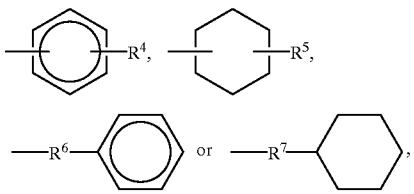

wherein $R^4$ represents a hydrogen atom, a $C_{1-12}$ straight- or branched-chain alkyl group, a $C_{2-12}$ straight- or branched-chain alkenyl group, a $C_{6-10}$ cycloalkyl group or a phenyl group; $R^5$ represents a $C_{1-12}$ straight- or branched-chain alkyl group, a $C_{2-12}$ straight- or branched-chain alkenyl group, a $C_{6-10}$ cycloalkyl group or a phenyl group; and $R^6$ and $R^7$ each represents a $C_{1-4}$ straight- or branched-chain alkylene group; with the proviso that when $R^4$ is a hydrogen atom, a $C_{1-12}$ alkyl group or a $C_{6-10}$ cycloalkyl group, $R^1$ is a residue formed by elimination of the two carboxyl groups of a $C_6$ or $C_8$ saturated aliphatic dicarboxylic acid;

(2) an amide compound of the formula:

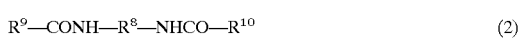

wherein $R^8$ represents a residue formed by elimination of the two amino groups of a $C_{4-28}$ alicyclic diamine, a $C_{4-14}$ 5- or 6- membered heterocyclic diamine containing 1 or 2 nitrogen or sulfur atoms in its ring or a $C_{6-28}$ aromatic diamine; $R^9$ and $R^{10}$ are the same or different and each represents a $C_{3-12}$ cycloalkyl group, a $C_{3-12}$ cycloalkenyl group, or a group of the formula:

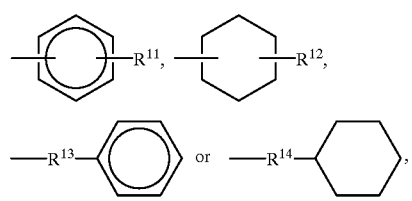

wherein $R^{11}$ represents a hydrogen atom, a $C_{1-12}$ straight- or branched-chain alkyl group, a $C_{2-12}$ straight- or branched-chain alkyl group, a $C_{6-10}$ cycloalkyl group or a phenyl group; $R^{12}$ represents a $C_{1-12}$ straight- or branched-chain alkyl group, a $C_{2-12}$ alkenyl group, a $C_{6-10}$ cycloalkyl group or a phenyl group; $R^{13}$ and $R^{14}$ each represents a $C_{1-4}$ straight- or branched-chain alkylene group; with the proviso that $R^8$ is not

and (3) an amide compound of the formula:

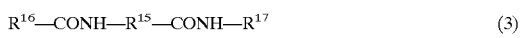

wherein $R^{15}$ represents a residue formed by elimination of one amino group and one carboxyl group of a $C_{2-29}$ saturated or unsaturated aliphatic amino acid, a $C_{7-13}$ saturated or unsaturated alicyclic amino acid or a $C_{7-15}$ aromatic amino acid; and $R^{16}$ and $R^{17}$ are the same or different and $R^{16}$ has the same meaning as $R^9$ or $R^{10}$ in the formula (2) and $R^{17}$ has the same meaning as $R^2$ or $R^3$ in the formula (1); said β-nucleating agent being present in an amount effective for providing an increased proportion of β-form crystals.

* * * * *